United States Patent
Moroshima et al.

(12)

(10) Patent No.: US 6,271,393 B1
(45) Date of Patent: Aug. 7, 2001

(54) PROCESS FOR PRODUCING $N^2$-(1(S)-CARBOXY-3-PHENYLPROPYL)-L-LYSYL-L-PROLINE

(75) Inventors: Tadashi Moroshima; Yoshifumi Yanagida; Yoshihide Fuse; Yasuyoshi Ueda, all of Hyogo (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/554,827

(22) PCT Filed: Sep. 22, 1999

(86) PCT No.: PCT/JP99/05189

§ 371 Date: Jul. 17, 2000

§ 102(e) Date: Jul. 17, 2000

(87) PCT Pub. No.: WO00/17229

PCT Pub. Date: Mar. 30, 2000

(30) Foreign Application Priority Data

Sep. 22, 1998 (JP) .................................................. 10-268676

(51) Int. Cl.[7] .................................................. C07D 207/06
(52) U.S. Cl. .................................................. 548/533
(58) Field of Search .................................................. 548/533

(56) References Cited

U.S. PATENT DOCUMENTS 5,616,727 * 4/1997 Kottenhahn .

FOREIGN PATENT DOCUMENTS

| 61-36297 | 2/1986 | (JP) . |
| 1-254651 | 10/1989 | (JP) . |
| 8-253497 | 10/1996 | (JP) . |
| 9-301938 | 11/1997 | (JP) . |
| 94/15957 | 7/1994 | (WO) . |

OTHER PUBLICATIONS

Blacklock, T. J. et al. "Synthesis of semisynthetic dipeptides using N–carboxyanhydrides and chiral induction on Raney nickel. A method practical for large scale" J. Org. Chem. (1988), vol. 53, No. 4, pp. 836–844.

* cited by examiner

Primary Examiner—Floyd D. Higel
Assistant Examiner—Andrea M D'Souza
(74) Attorney, Agent, or Firm—Sughrue, Mion, Zinn, Macpeak & Seas, PLLC

(57) ABSTRACT

The process for producing $N^2$-(1(S)-carboxy-3-phenylpropyl)-L-lysyl-L-proline in a simple, efficient and industrially advantageous manner, including the following steps:

1) subjecting $N^2$-(1(S)-alkoxycarbonyl-3-phenylpropyl)-$N^6$-trifluoroacetyl-L-lysyl-L-proline (1) to alkali hydrolysis in a mixed solution composed of water and a hydrophilic organic solvent using an inorganic base in an amount of n molar equivalents (n ≧ 3) per mole of the above compound (1), 2) neutralizing the hydrolysis product using an inorganic acid in an amount of (n − 1) to n molar equivalents (n ≧ 3) to form a compound (2) and removing the inorganic salt formed by causing the same to precipitate out from a solvent system suited for decreasing the solubility of the inorganic salt, and 3) causing the compound (2) existing in the mixture after removal of the inorganic salt to crystallize out at the isoelectric point thereof and thereby recovering the compound (2) in the form of crystals while retaining the salts including the trifluoroacetic acid-derived organic acid salt in a state dissolved in the mother liquor.

20 Claims, No Drawings

PROCESS FOR PRODUCING $N^2$-(1(S)-CARBOXY-3-PHENYLPROPYL)-L-LYSYL-L-PROLINE

This is a §371 application of PCT/JP99/05189, filed Sep. 22, 1999.

TECHNICAL FIELD

The present invention relates to a process for producing high-quality N2- (1(S) -carboxy-3-phenylpropyl) -L-lysyl-L- proline of the formula (2) (hereinafter also referred to as lisinopril (2)) in high yields and in an economically advantageous manner on a commercial scale. N2-(1(S)- carboxy-3phenylpropyl)-L-lysyl-L-proline (2) (lisinopril) is a compound very useful as an antihyertensive agent.

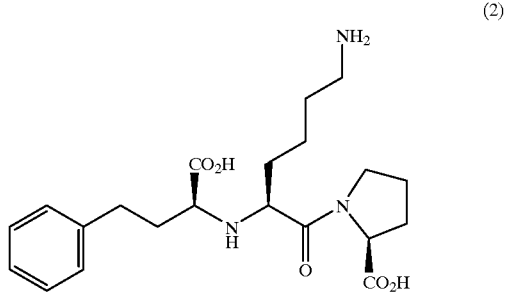

(2)

BACKGROUND ART

Lisinopril (2) can readily be synthesized by hydrolyzing an N2- (1 (S)-alkoxycarbonyl-3-phenylpropyl)-N6; trifluoroacetyl-L-lysyl-L-proline of the general formula (1)

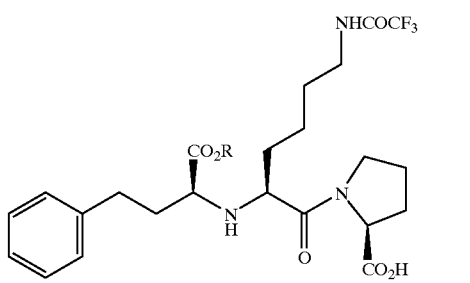

(1)

wherein R represents an alkyl group, using a base in the presence of water and then neutralizing all the basic components in the hydrolysis mixture using an acid. On that occasion, however, it is necessary, for isolating lisinopril (2), to separate lisinopril (2) from salts (salt of trifluoroacetic acid resulting from hydrolysis and salt formed from the base and acid used) which coexist in large amounts.

In that regard, the process disclosed in EP 168769 or *J. Org. Chem.*, 53, 836 –844 (1988), for example, comprises hydrolyzing N2- (1 (S)-ethoxycarbonyl-3-phenylpropyl)-N6- trifluoroacetyl L-lysyl-L-proline with sodium hydroxide, acidifying the hydrolysis mixture with hydrochloric acid, removing all the resulting coexisting substances such as sodium chloride, trifluoroacetic acid and/or the sodium salt thereof by treatment on an ion exchange column, concentrating the organic base-containing eluate (eluent being aqueous ammonia or pyridine-water), adjusting the concentrate to the isoelectric point with hydrochloric acid and recovering lisinopril (2) by causing the same to crystallize out from the final water-ethanol mixture solution containing the amine salt formed upon the above adjustment to isoelectric point.

The above process, however, is not only complicated in operation but also poor in productivity since it is necessary to remove a large amount of salts by ion exchange treatment and the eluate is dilute, so that large-scale equipment is required and a long period and a large quantity of heat energy are wasted for the concentration of the eluate. Furthermore, the quantity of waste water to be treated, inclusive of the portion resulting from regeneration treatment of the ion exchange column, is enormous. In addition, the ion exchange column potentially poses a serious problem, namely it may readily allow various microorganisms to grow therein. In view of these and other drawbacks, the above process can hardly be said to be an advantageous one from the industrial production viewpoint.

In an another example, as disclosed in Japanese Kokai Publication *Hei*-08-253497, for instance, N2-(1(S)-ethoxycarbonyl 3-phenylpropyl) -N6-trifluoroacetyl-L-lysyl- L-proline is hydrolyzed with tetrabutylammonium hydroxide, which is an organic base, the hydrolysis mixture is then neutralized with trifluoroacetic acid, which is an organic acid, so that an organic salt, namely tetrabutylammonium trifluoroacetate, alone may be formed as the salt component, and lisinopril (2) is recovered by causing the same to crystallize out at the isoelectric point thereof from a mixed solvent system composed of water and ethanol in the presence of the whole amount of the organic salt.

However, the process just mentioned above, too, can hardly be said to be advantageous from the viewpoint of economy, safety and industrial practice because of the use of special reagents such as tetrabutylammonium hydroxide and trifluoroacetic acid.

Thus, in the prior art, no process is known for separating N2- (1 (S) -carboxy-3-phenylpropyl)-L-lysyl-L-proline (2) from the salt(s) mentioned above in a simple and efficient and industrially advantageous manner.

The present invention has for its object to provide a simple, efficient and industrially advantageous process for separating the salt and lisinopril (2) formed by alkali hydrolysis of N2- (1(S)-alkoxycarbonyl-3-phenylpropyl)-N6- trifluoroacetyl L-lysyl-L-proline and subsequent neutralization from the reaction mixture.

SUMMARY OF THE INVENTION

First, the present inventors investigated the feasibility of the process comprising hydrolyzing N2-(1(S)-alkoxycarbonyl 3-phenylpropyl) -N6-trifluoroacetyl-L-lysyl- L-proline with the inorganic base sodium hydroxide and neutralizing the reaction mixture with the inorganic acid hydrochloric acid or organic acid trifluoroacetic acid, under formation of the inorganic salt sodium chloride or organic acid salt sodium trifluoroacetate, and recovering N2-(1(S)-carboxy 3-phenylpropyl) -L-lysyl-L-proline by causing the same to crystallize out from a solvent system such as water or ethanol while retaining a large amount of such salts dissolved therein. As a result, it was revealed that the yield in recovering crystals of lisinopril (2) and the extent of removal of salts are both unsatisfactory. It was also found that the presence of such salts in large amounts retards the nucleation and crystal growth of lisinopril (2) and causes deterioration in crystal property by which the filterability is reduced. It was thus found that this approach has its limits.

When, however, the salt concentration was reduced for crystallization of lisinopril (2), a tendency was shown toward improvements in the above aspects. It was supposed that reducing salt concentration in advance is necessary and helpful for recovering lisinopril (2) by crystallization. As a result of further intensive investigations made from that point of view, the inventors came to believe that, from the viewpoint of eliminating two different kinds of salts, namely the organic acid salt formed by the trifluoroacetic acid resulting from hydrolysis and the inorganic base used for hydrolysis and the inorganic salt formed upon neutralization from the inorganic base and the inorganic acid used, optimum separating method shouldbe established for each salt according to such properties as solubility in solvent and interaction with lisinopril (2).

Thus, the present invention provides a process for producing N2-(1(S)-carboxy-3-phenylpropyl)-L-lysyl-L-proline of the formula (2):

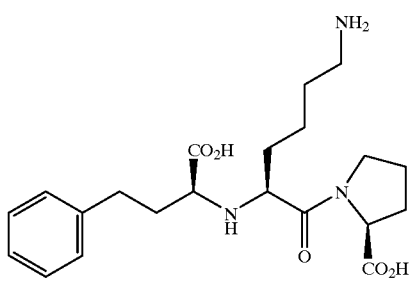

(2)

from an N2- (1(S)-alkoxycarbonyl-3-phenylpropyl)-N6-trifluoroacetyl L-lysyl-L-proline of the general formula (1):

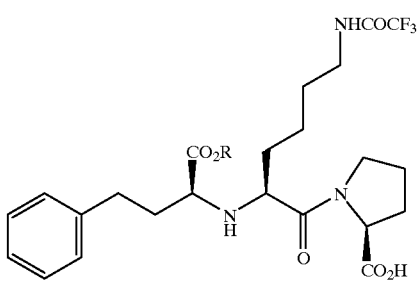

(1)

wherein R represents an alkyl group, which comprises:

the first step: subjecting the N2-(1(S)- alkoxycarbonyl 3-phenylpropyl)-N6-trifluoroacetyl-L-lysyl- L-proline (1) to alkali hydrolysis in a solvent system being selected from among mixed solution composed of water and a hydrophilic organic solvent, and water using an inorganic base in an amount of n molar equivalents (n ≧ 3) per mole of the above compound (1), the second step: neutralizing the hydrolysis product using an inorganic acid in an amount of (n − 1) to n molar equivalents (n ≧ 3) and separating and removing the inorganic salt formed from the above inorganic base and inorganic acid in the reaction mixture by causing the same to precipitate out from a solvent system suited for decreasing the solubility of the inorganic salt, said solvent system being selected from a hydrophilic organic solvent, a mixed solvent composed of water and a hydrophilic organic solvent, and water, and the third step: causing the lisinopril (2) existing in the mixture after removal of the inorganic salt to crystallize out from a solvent system at the isoelectric point thereof, said solvent system being selected from a hydrophilic organic solvent, a mixed solvent composed of water and a hydrophilic organic solvent, and water, and thereby recovering the lisinopril (2) in the form of crystals while retaining the salts mainly comprising the trifluoroacetic acid-derived organic acid salt in a state dissolved in the mother liquor.

The process of the present invention makes it possible to separate and recover lisinopril (2) with a reduced salt content from a lisinopril (2)- and salt-containing mixture in a simple and efficient manner.

DETAILED DESCRIPTION OF THE INVENTION

In the first step, each mole of an N2-(1 (S) alkoxycarbonyl-3-phenylpropyl)-N6-trifluoroacetyl-L-lysyl L-proline (1) is hydrolyzed using n molar equivalents (n ≧ 3) of an inorganic base in a solvent system selected from among a mixed solvent composed of water and a hydrophilic organic solvent, and water.

In the general formula (1):

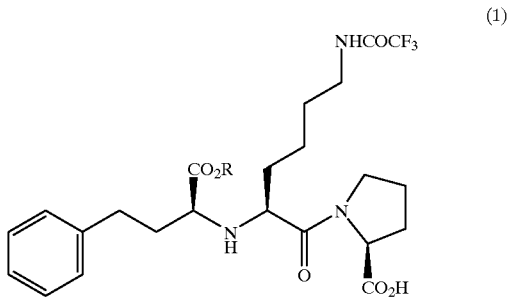

(1)

(R being an alkyl group), which represents the N2- (1(S) -alkoxycarbonyl-3-phenylpropyl) N6-trifluoroacetyl-L-lysyl-L-proline, R is a group hydrolyzable under alkaline conditions, preferably an alkyl group, more preferably an alkyl group containing 1 to 4 carbon atoms, still more preferably an ethyl group.

The N2- (1(S)-alkoxycarbonyl-3-phenylpropyl)-N6-trifluoroacetyl L-lysyl-L-proline (1) to be used can be prepared by the methods described, for example, in Japanese Kokai Publication *Hei*-01-254651, Japanese Kokai Publication *Hei*-05-201882, EP 168769 or *J. Org. Chem.*, 53, 836-844 (1988).

The inorganic base to be used for hydrolyzing the N2-(1 (S)-alkoxycarbonyl 3-phenylpropyl)-N6-trifluoroacetyl-L-lysyl-L-proline is not particularly restricted but includes, among others, hydroxides and carbonates of alkali metals or alkaline earthmetals. As specific examples of such base, there may be mentioned, among others, alkali metal hydroxides such as sodium hydroxide and potassium hydroxide; alkali metal carbonates such as sodium carbonate and potassium carbonate; and alkaline earth metal hydroxides such as magnesium hydroxide and calcium hydroxide. Other inorganic bases may also be used. Among them, basic sodium compounds and basic potassium compounds are preferred. From the operability viewpoint, these bases are preferably used in the form of aqueous solutions. It is generally advantageous to use them in the form of aqueous solutions having a concentration of 5 to 50% by weight, preferably 20 to 48% by weight. These bases may be used singly or two or more of them may be used in combination. For example, the first step can preferably be carried out using one molar equivalent of sodium hydrogencarbonate and (n − 1) molar equivalents (n ≧ 3) of sodium hydroxide.

The inorganic base using in an amount of n molar equivalents is required for the hydrolysis of the N2-(1 (S)-alkoxycarbonyl 3-phenylpropyl)-N6-trifluoroacetyl-L-lysyl-L-proline (1). Generally, the base is used in an amount of not less than 3 molar equivalents (n ≧ 3) relative to the N2- (1(S) -alkoxycarbonyl 3-phenylpropyl) -N6-trifluoroacetyl-L-lysyl-L-proline (1). The inorganic base may be added all at once from the beginning, or successively or portionwise so that the pH may be maintained at a selected value or varied stepwise during hydrolysis. The final pH of the reaction mixture is preferably made 12 or higher.

While the hydrolysis can generally be conducted in an aqueous system, it is also possible to conduct the hydrolysis in a mixed solution composed of water and a hydrophilic organic solvent which contains the other organic solvents in an amount having no adverse influence. The hydrophilic organic solvent to be contained is not particularly restricted. Generally, there may be mentioned monohydric alcohols containing 1 to 4 carbon atoms, such as methanol, ethanol, propanol, isopropanol and t-butanol and, in that case, it is preferred that R in the general formula (1) representing the N2-(1(S)- alkoxycarbonyl 3-phenylpropyl)-N6-trifluoroacetyl-L-lysyl- L-proline to be used is the same as the alkyl group of the above-mentioned alcohol. Ethanol can be used more preferably and, in that case, it is preferred that R in general formula (1) be an ethyl group. When a mixed solvent composed of water and a hydrophilic organic solvent, in particular a mixed solvent composed of water and such an alcohol as mentioned above, is used, the mixing ratio is generally 1:1 to 1: 99, preferably 1: 1 to 1:9, more preferably 1:1 to 1:7, by weight.

As regards the operation temperature in the hydrolysis step, an especially high temperature is not required. Practically, the reaction can be carried out generally at a temperature not higher than 70 °C, preferably not higher than 60 °C at which the solvent system will not be frozen, preferably at 0 to 50 °C, more preferably at about 30 °C.

In the second step, the reaction mixture from the first step is neutralized using an inorganic acid in an amount of (n − 1) to n molar equivalents (n ≧ 3), and the inorganic salt formed in the resulting mixture from the above inorganic base and inorganic acid is removed by causing the same to precipitate out from a solvent system, which is suited for reducing the solubility of the inorganic salt, as selected from among a hydrophilic organic solvent, a mixed solvent composed of water and a hydrophilic organic solvent, and water.

The amount of the inorganic acid for neutralization is basically (n − 1) molar equivalents relative to the amount (n molar equivalents) of the inorganic base used in the first step to hydrolyze the N2- (1 (S)-alkoxycarbonyl-3-phenylpropyl)- N6trifluoroacetyl-L-lysyl-L-proline. This is because one mole of the inorganic base is consumed in hydrolyzing the trifluoroacetyl group and the resulting trifluoroacetic acid and the inorganic base form an organic acid salt. Therefore, when the inorganic acid is used in that amount, (n − 1) molar equivalents of the inorganic salt is formed in addition to one molar equivalent of the organic acid salt formed from trifluoroacetic acid and the inorganic base, and thus the whole of the inorganic base component used is neutralized to form the salts. On that occasion, the pH of the mixture is in the vicinity of the isoelectric point of lisinopril (2) and the pH value is generally about 5.2 ± 0.4.

While the inorganic acid to be used is not particularly restricted, the use of a strong acid is preferred from the practicability viewpoint. Thus, hydrochloric acid and sulfuric acid are preferred among others, and hydrochloric acid is particularly preferred. These inorganic acids may be used singly or two or more of them may be used in combination. While these inorganic acids can be used as they are, they may be used as solutions prepared by dilution with an aqueous medium.

When an inorganic acid stronger in acidity than trifluoroacetic acid, preferably hydrochloric acid, is used, acidification can be advantageously carried out to an extent exceeding the isoelectric point and the amount of the inorganic acid to be used, based on the inorganic base used (n molar equivalents), is within the range of over (n − 1) up to n molar equivalents, whereby the same molar equivalents of the inorganic salt as the inorganic acid component used can be formed. On that occasion, the amount of the trifluoroacetic acid component not involved in salt formation with the inorganic base component increases, so that the pH of the mixture becomes lower than the isoelectric point of lisinopril (2).

On the contrary, when the inorganic acid is used in an amount outside the range of not less than (n − 1) molar equivalents to n molar equivalents or when an acid weaker than trifluoroacetic acid is used in an amount of more than (n − 1) molar equivalents but not more than n molar equivalents, the inorganic base component or inorganic acid component is not wholly removed in this step but partly remains and, in the next step of recovery of lisinopril (2) by crystallization, further neutralization becomes necessary and troubles may unfavorably arise, for example the salt formed on that occasion may contaminate the desired crystals or may worsen the crystallizability of the desired product.

In the above procedure, the time over which the whole amount of the inorganic acid is to be added is not particularly restricted but generally is not less than a quarter of an hour, usually not less than a third of an hour, preferably not less than half an hour and, from the viewpoint of productivity or the like, it is generally not more than 20 hours, usually not more than 10 hours, preferably not more than 5 hours.

As regards the solvent system suited for reducing the solubility of the inorganic salt and inducing the precipitation thereof formed in the mixture resulting from neutralization, the use of a hydrophilic organic solvent as a poor solvent is effective and it is also preferably practicable to make a mixed solvent system composed of a hydrophilic organic solvent and water or, further, make a replacement of the medium by a hydrophilic organic solvent. The organic solvent to be selected from such viewpoints is not particularly restricted but specifically includes, among others, monohydric alcohols containing 1 to 4 carbon atoms such as methanol, ethanol, propanol, isopropanol and tert-butanol; acetone, tetrahydrofuran, acetonitrile and the like. Other hydrophilic organic solvents may also be used. In particular, monohydric alcohols containing 1to 4carbon atoms are preferred and, for minimizing the possible adverse effects on the human body in the case of a trace amount of the solvent being brought into the final product, ethanol is particularly advantageous. These may be used singly or two or more of them may be used combinedly. Certain inorganic salt species may be eliminated by precipitation from water as well.

The amount of the hydrophilic organic solvent to be used in the above procedure cannot be specified since it depends on the hydrophilic organic solvent species employed and the inorganic salt species to be eliminated, among others. When an organic solvent is used as a poor solvent for the inorganic salt, for instance, the percent elimination of the inorganic salt increases when the percentage of the organic solvent is increased. From such a viewpoint, the weight ratio between water and the hydrophilic organic solvent is generally 4:1 to 1:99, preferably 1:1 to 1:99, more preferably 3:7 to 1:99. Certain inorganic salt species can be precipitated from water as well. As specific examples of such inorganic salt, there may be mentioned potassium sulfate and calcium sulfate, among others. The inorganic salt species can be selected on the basis of solubilities in water and organic solvents, referring to monographs and the like in the relevant field of art or based on simple experiments. The inorganic salt species selected can be formed by selecting the combination of inorganic base and inorganic acid.

While the inorganic salt formed precipitates out rapidly, lisinopril (2) requires a long period for nucleation and crystal growth, so that it is possible to cause preferential precipitation of the inorganic salt for separation and removal thereof. Further, selection of more suited conditions is preferred; for example, the temperature is preferably maintained at a low level, for example 0 to 30°C.

In the above procedure, it is more preferred and efficient to use an inorganic acid stronger in acidity than trifluoroacetic acid as the inorganic acid for neutralization in an amount within the range of over (n − 1) up to n molar equivalents relative to the inorganic base (n molar equivalents) to thereby effect acidification to an extent exceeding the isoelectric point. In particular, in this range, the use of the inorganic acid in an increased amount enhances the effect and the use of the same molar equivalents (n molar equivalents) of the inorganic acid as the inorganic base is most preferred. By this, it is possible to cause preferential precipitation of the inorganic salt and the subsequent separation thereof by filtration, with allowing no or almost no precipitation of lisinopril (2), as a result of a reduction in rate of nucleation and crystal growth of lisinopril (2) and an improvement in solubility thereof.

The inorganic salt precipitate formed from the resulting mixture in this step can be separated/removed in a simple and easy manner by a common solid-liquid separation procedure such as centrifugal separation or pressure filtration.

In the third step, lisinopril (2) existing in the resultant mixture after elimination of the inorganic salt is allowed to crystallize out from a hydrophilic organic solvent, a mixed solvent composed of water and an organic solvent, or water, at the isoelectric point thereof, whereby crystals of lisinopril (2) are recovered while allowing the salts, the majority of which is a trifluoroacetic acid-derived organic acid salt, to remain dissolved in the mother liquor.

In allowing lisinopril (2) existing in the mixture obtained after elimination of the inorganic salt in the second step to crystallize out under isoelectric point conditions, no particular treatment is generally required if the mixture is already at the isoelectric point in the neutralization stage in the preceding step as a result of the use of (n − 1) molar equivalents of the inorganic acid. When the mixture is in an acidified condition exceeding the isoelectric point as a result of the use of the inorganic acid in an amount of more than (n − 1) molar equivalents to n molar equivalents, it is judicious to attain the isoelectric point using a base so as to increase the percentage of crystallization of lisinopril (2). In that procedure, the base is generally used in an amount of [(number of molar equivalents of the inorganic acid used) minus (n − 1)] molar equivalents. The neutral salt formed on that occasion is mainly composed of a trifluoroacetic acid-derived organic acid salt, as mentioned above, and it is thus possible to cause effective crystallization of lisinopril (2), followed by efficient separation and recovery thereof, while retaining the above salt in a state dissolved in the crystallization solvent for lisinopril (2).

The base to be used in adjusting the mixture to the isoelectric point is not particularly restricted but may be selected from among those inorganic bases to be used in the first step of hydrolyzing. In addition, alkali metal hydrogencarbonates such as sodium hydrogencarbonate and potassium hydrogencarbonate and alkaline earth metal carbonates such as magnesium carbonate and calcium carbonate, for instance, are also suited for use. Further, aqueous ammonia and organic bases, for example amines such as triethylamine and pyridine, may also be used. However, basic compounds of sodium and basic compounds of potassium are preferred. These may be used singly or two or more of them may be used combinedly.

The crystallization solvent for lisinopril (2) to be used in this step is, for example, water, a hydrophilic organic solvent or a mixture thereof. In particular, the use of a mixed solvent composed of water and a hydrophilic organic solvent is preferred from the viewpoint of improving the removability of the organic acid salt derived from trifluoroacetic acid and the base and the crystallizability of lisinopril (2). The hydrophilic organic solvent to be used can be replaced with one selected from among those hydrophilic organic solvent to be used in the second step. However, the use of the same kind of solvent system as used in the second step is preferred, since such use is simple and economical, hence advantageous. Replacement of the hydrophilic organic solvent with water is also practicable and preferred.

While the concentration of lisinopril (2) for crystallization thereof cannot be particularly specified since it depends on the operation temperature, the base species used and the amount thereof, the composition of the crystallization solvent and the concentration of the coexisting salt (s), it is preferred, for further improvement in crystallization yield in the stage of crystallization, that the solution has a concentration as high as possible. From the viewpoint of preventing crystals from being contaminated by the salt (s), however, it is also important that the concentration is not too high. Practically, the lower concentration limit is preferably set at a level not lower than 5%, more preferably not lower than 10%, while the upper concentration limit is preferably set at a level not higher than 40%, more preferably not higher than 30%. Usually, the crystallization can judiciously be effected at a concentration of about 10 to 25%.

The concentration of the salts, coexisting in the mixture on the occasion of crystallization of lisinopril (2) and mainly containing the trifluoroacetic acid-derived organic acid salt, is also important from the viewpoint of promoting good crystal growth. Although it depends on the operation concentration, temperature and procedure as well as on the coexisting neutral salt species, among others, hence cannot be specified in general terms, the salt concentration is generally to be not higher than 15% by weight, preferably not higher than 10% by weight, more preferably not higher than 8% by weight.

The temperature to be employed in the crystallization of lisinopril (2) cannot be particularly specified since it depends on the composition of the crystallization solvent, the procedure and other factors. Practically, however, the third step is carried out at a temperature which is not higher than the boiling point of the crystallization solvent but at which the solvent will not freeze. While an especially high temperature is not required, to raise the temperature at the time of crystallization favorably leads to increased rates of nucleation and crystal growth of lisinopril (2). From such viewpoint, the operation is preferably carried out at a temperature of 40 to 70 °C, more preferably at about 50°C. The yield of crystals can be increased by finally cooling to not higher than 20°C, preferably not higher than 10°C.

The resulting crystals of lisinopril (2) can be readily recovered by an ordinary solid-liquid separation procedure, such as centrifugal separation or pressure filtration, without any particular procedure. Thus, high-quality crystals can be obtained efficiently and in high yields.

When, in the practice of the present invention, N2-(1(S)-ethoxycarbonyl 3-phenylpropyl) -N6-trifluoroacetyl-L-lysyl L-proline is used as the reaction substrate, a basic compound of sodium as the inorganic base and hydrochloric acid as the inorganic acid, for instance, the mode of embodiment will be as follows:

In the first step, the hydrolysis is conducted in water or a mixture of water and ethanol using n molar equivalents (n ≧ 3) of the basic compound of sodium as the inorganic base;

in the second step, the reaction mixture is neutralized using n molar equivalents of hydrochloric acid as the inorganic acid and the resulting sodium chloride is caused to efficiently precipitate from ethanol or a mixture of ethanol and water and removed by filtration; and in the third step, one molar equivalent of the basic compound of sodium is added to the mixture after elimination of sodium chloride and, while the resulting sodium trifluoroacetate is retained in a state dissolved in the resulting mixture of ethanol and water, lisinopril (2) is efficiently caused to crystallize out, followed by collection of the crystals.

In another preferred embodiment in which a basic compound of potassium, for example, is used as the inorganic base and sulfuric acid as the inorganic acid, the process will be as follows:

In the first step, the hydrolysis is carried out in water or a mixture of water and ethanol using n molar equivalents (n ≧ 3) of the basic compound of potassium as the inorganic base;

in the second step, the reaction mixture is neutralized using (n - 1) molar equivalents of sulfuric acid as the inorganic acid to thereby adjust the mixture to the isoelectric point of lisinopril (2), and the resulting potassium sulfate is caused to efficiently precipitate from water or a mixture of water and ethanol and removed by filtration; and in the third step, while the potassium trifluoroacetate is retained in a state dissolved in water or a mixture of water and ethanol, lisinopril (2) is allowed to efficiently crystallize out, followed by collection of the crystals.

BEST MODES FOR CARRYING OUT THE INVENTION

The following examples illustrate the present invention in further detail. They are, however, by no means limitative of the scope of the invention.

For purity testing, HPLC was performed and the purity was calculated by the absolute working curve method. The water content was determined by the Karl Fischer method. The sodium chloride content was determined using an ion chromatograph. The HPLC conditions were as follows:
[HPLC]
- Column: Capsule Pack UG-120 (trademark; 4.6 mm x 25 cm; product of Shiseido Co.)
- Solvent: 60 mM $KH_2PO_4$(pH 2.8)/$CH_3CN$ (90:10 (by volume))
- Flow rate: 1.0 ml/min
- Temperature: 50 °C
- Detection: UV 210 nm

EXAMPLE 1

N2- (1 (S) -Ethoxycarbonyl-3-phenylpropyl)-N6-trifluoroacetyl-L-lysyl-L-proline (1) (32.0 g) and 25.9 g of 30% by weight aqueous solution of NaOH were mixed up and the hydrolysis reaction was allowed to proceed with stirring for about 4 hours. To the reaction mixture was added 20.1 g of concentrated hydrochloric acid to make the pH 2.8 ± 0.5. The resulting solution was two-fold diluted with ethanol and the diluted solution was concentrated to the original volume. By repeating this dilution/concentration procedure, the concentration of water was reduced to 4 ± 2% by weight. To this solution was added ethanol to make the concentration of lisinopril (2) 22 ± 2% by weight. The resulting mixture was stirred for 1 hour. The precipitate was filtered off and washed with 30 ml of ethanol. To the resulting filtrate was added 16.1 g of a 15% aqueous solution of NaOH (the pH becoming 5.8). This solution was warmed to 45 °C, seed crystals were added, and the mixture was stirred for 3 hours, then cooled to 5 °C over 2 hours and further stirred for 12 hours. The precipitate crystals were collected by filtration and washed with three 30-ml portions of 70% by weight ethanol cooled to 5 °C. The crystals obtained were subjected to vacuum drying (20 to 50 °C, from 30 mm Hg to 1 mm Hg), to give 22.7 to 23.5 g (yield: 85 to 88%) of lisinopril (2) dihydrate. The purity was not less than 99%, the water content was 8.2% and the sodium chloride content was not more than 0.1% by weight.

EXAMPLE 2

N2- (1(S)-Ethoxycarbonyl-3-phenylpropyl)-N6- trifluoroacetyl L-lysyl-L-proline (1) (32.0 g) and 25.9 g of 30% by weight aqueous solution of NaOH were mixed up and the hydrolysis reaction was allowed to proceed with stirring for about 4 hours. To the reaction mixture was added 13.9 g of concentrated hydrochloric acid to make the pH 5.2 ± 0.2. The resulting solution was two-fold diluted with ethanol and the diluted solution was concentrated to the original volume. By repeating this dilution/concentration procedure, the concentration of water was reduced to 4 ± 2% by weight. To this solution was added ethanol to make the concentration of lisinopril (2) 22 ± 2% by weight. The resulting mixture was stirred for 1 hour. The precipitate was filtered off and washed with 30 ml of ethanol. To the resulting filtrate was added 15.0g of water. This solution was warmed to 45 °C, seed crystals were added, and the mixture was stirred for 3 hours, then cooled to 5 °C over 2 hours and further stirred for 12 hours. The precipitate crystals were collected by filtration and washed with three 30-ml portions of 70% by weight ethanol cooled to 5 °C. The crystals obtained were subjected to vacuum drying (20 to 50 °C, from 30 mm Hg to 1 mm Hg), to give 22.7 to 23.5 g (yield: 85 to 88%) of lisinopril (2) dihydrate. The purity was not less than 99%, the water content was 8.2% and the sodium chloride content was not more than 0.1% by weight.

EXAMPLE 3

N2- (1(S)-Ethoxycarbonyl-3-phenylpropyl)-N6- trifluoroacetyl L-lysyl-L-proline (1) (32.0 g) and 25.9 g of 30% by weight aqueous solution of NaOH were mixed up and the hydrolysis reaction was allowed to proceed with stirring for about 4 hours. To the reaction mixture was added 20.1 g of concentrated hydrochloric acid to make the pH 2.8 ± 0.5. The resulting solution was two-fold diluted with ethanol and the diluted solution was concentrated to the original volume. By repeating this dilution/concentration procedure, the concentration of water was reduced to 3 ± 2% by weight. To this solution was added 5.0 g of a 48% (by weight) aqueous solution of NaOH (the pH becoming 5.7), followed by further addition of ethanol to make the concentration of lisinopril (2) 22 ± 2% by weight. The resulting mixture was stirred for 1 hour. The precipitate was filtered off and washed with 30 ml of ethanol. To the resulting filtrate was added 12.0 g of water. This solution was warmed to 45 °C, seed crystals were added, and the mixture was stirred for 3 hours, then cooled to 5 °C over 2 hours and further stirred for 12 hours. The precipitate crystals were collected by filtration and washed with three 30-ml portions of 70% by weight ethanol cooled to 5 °C. The crystals obtained were subjected to vacuum drying (20 to 50°C, from 30 mm Hg to 1 mm Hg), to give 22.7 to 23.5 g (yield: 85 to 88%) of lisinopril (2) dihydrate. The purity was not less than 99%, the water content was 8.2% and the sodium chloride content was not more than 0.1% by weight.

EXAMPLE 4

N2-(1(S)-Ethoxycarbonyl-3-phenylpropyl)-N6-trifluoroacetyl L-lysyl-L-proline (1) (100.0 g) was added to a mixed solution composed of 50.4 g of 48% by weight aqueous solution of NaOH and 39.3 g of ethanol, and the hydrolysis reaction was allowed to proceed with stirring for about 4 hours. To the reaction mixture was added 62.9 of concentrated hydrochloric acid. Ethanol was added to the resulting solution to make the lisinopril (2) concentration 8 ± 2% by weight, and stirring was further continued for 1 hour. The precipitate was filtered off and washed with two 40-ml portions of ethanol. To the resulting filtrate was added 75.5 g of 10% by weight aqueous solution of NaOH (the pH becoming 6.0). This solution was warmed to 45 °C, seed crystals were added, and the mixture was stirred for 3 hours, then cooled to 5 °C over 2 hours and further stirred for 12 hours. The precipitate crystals were collected by filtration and washed with three 30-ml portions of 70% by weight ethanol cooled to 5 °C. The crystals obtained were subjected to vacuum drying (20 to 50 °C, from 30 mm Hg to 1 mm Hg), to give 65.9 to 70.0 g (yield: 79 to 84%) of lisinopril (2) dehydrate. The purity was not less than 99%, the water content was 8.2% and the sodium chloride content was not more than 0.1% by weight.

EXAMPLE 5

N2- (1(S)-Ethoxycarbonyl-3-phenylpropyl)-N6-trifluoroacetyl L-lysyl-L-proline (1) (30.0 g) and 17.0 g of 38% by weight aqueous solution of KOH were mixed up and the hydrolysis reaction was allowed to proceed with stirring for about 4 hours. To the reaction mixture was added 6.9 g of concentrated hydrochloric acid to make the pH 5.2 ± 0.5, and stirring was further continued for 1 hour. The precipitate was filtered off and washed with 15 ml of water. The resulting filtrate were warmed to 45 °C, seed crystals were added, and the mixture was stirred for 3 hours, then cooled to 5 °C over 2 hours and further stirred for 12 hours. The precipitate crystals were collected by filtration and washed with three 15-ml portions of water cooled to 5 °C. The crystals obtained were subjected to vacuum drying (20 to 50 °C, from 30 mm Hg to 1 mm Hg), to give 20.0 to 21.3 g (yield: 80 to 85%) of lisinopril (2) dihydrate. The purity was not less than 99%, the water content was 8.2% and the potassium sulfate content was not more than 0.1% by weight.

INDUSTRIAL UTILIZABILITY

The process of the present invention makes it possible to produce N2-(1(S)-carboxy-3-phenylpropyl) -L-lysyl-L- proline in a simple, efficient and industrially advantageous manner.

What is claimed is:
1. A process for producing N2-(1(S)-carboxy-3-phenylpropyl) L-lysyl-L-proline of the formula (2):

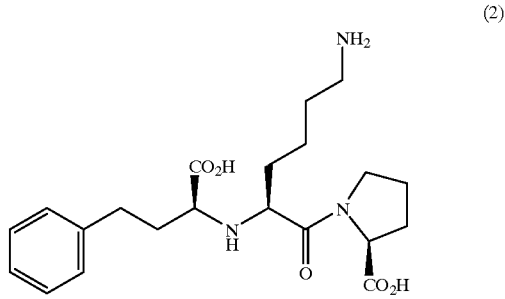

from an N2- (1(S)-alkoxycarbonyl-3-phenylpropyl)-N6-trifluoroacetyl L-lysyl-L-proline of the general formula (1):

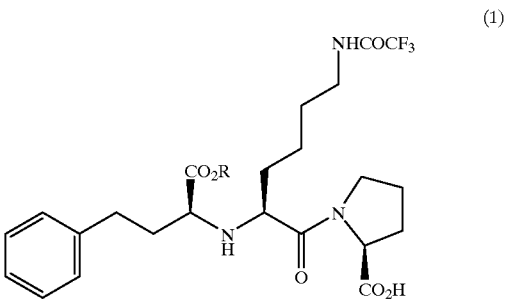

wherein R represents an alkyl group,
  which comprises:
    the first step: subjecting the N2-(1(S)-alkoxycarbonyl 3-phenylpropyl) -N6-trifluoroacetyl-L-lysyl-L-proline (1) to alkali hydrolysis in a solvent system being selected from among a mixed solution composed of water and a hydrophilic organic solvent, and water using an inorganic base in an amount of n molar equivalents (n ≧ 3) per mole of the above compound (1),
    the second step: neutralizing the hydrolysis product using an inorganic acid in an amount of (n − 1) to n molar equivalents (n ≧ 3) and
    separating and removing the inorganic salt formed from the above inorganic base and inorganic acid in the reaction mixture by causing the same to precipitate out from a solvent system suited for decreasing the solubility of the inorganic salt,
    said solvent system being selected from a hydrophilic organic solvent, a mixed solvent composed of water and a hydrophilic organic solvent, and water, and
    the third step: causing the N2-(1(S)-carboxy-3-phenylpropyl) L-lysyl-L-proline (2) existing in the mixture after removal of the inorganic salt to crystallize out from a solvent system at the isoelectric point thereof,
    said solvent system being selected from a hydrophilic organic solvent, a mixed solvent composed of water and a hydrophilic organic solvent, and water, and
    thereby recovering the N2- (1(S)-carboxy-3-phenylpropyl) L-lysyl-L-proline (2) in the form of crystals while retaining the salts mainly comprising the trifluoroacetic acid-derived organic acid salt in a state dissolved in the mother liquor.

2. The process for producing according to claim 1, wherein the inorganic base used in the first step is an alkali metal hydroxide, an alkali metal carbonate or an alkaline earth metal hydroxide.

3. The process for producing according to claim 2, wherein the inorganic base used in the first step is a basic compound of sodium or a basic compound of potassium.

4. The process for producing according to claim 1, wherein, in the second step, the inorganic acid is used in an amount within the range of over (n – 1) up to n molar equivalents (n ≧ 3) and, in the third step, the mixture after removal of the inorganic salt is adjusted to the isoelectric point using a base in an amount of molar equivalents.

5. The process for producing according to claim 4, wherein, in the second step, the inorganic acid is used in an amount of n molar equivalents (n ≧ 3) and, in the third step, the mixture after removal of the inorganic salt is adjusted to the isoelectric point using one mole equivalent of a base.

6. The process for producing according to claim 4, wherein, in the third step, the base used for the adjustment to the isoelectric point is an inorganic base selected from among alkali metal hydroxides, alkali metal carbonates, alkali metal hydrogencarbonates, alkaline earth metal hydroxides and alkaline earth metal carbonates.

7. The process for producing according to claim 6, wherein, in the third step, the base used for the adjustment to the isoelectric point is a basic compound of sodium or a basic compound of potassium.

8. The process for producing according to claim 1, wherein the inorganic acid used in the second step is hydrochloric acid or sulfuric acid.

9. The process for producing according to claim 1, wherein the precipitation of the inorganic salt in the second step and the crystallization of N2-(1(S)-carboxy-3-phenylpropyl) L-lysyl-L-proline (2) in the third step are effected from a mixed solvent system composed of water and a hydrophilic organic solvent.

10. The process for producing according to claim 9, wherein the weight ratio of water and a hydrophilic organic solvent in the mixed solvent is 4:1 to 1:99.

11. The process for producing according to claim 1, wherein the hydrophilic organic solvent is a monohydric alcohol containing 1 to 4 carbon atoms.

12. The process for producing according to claim 11, wherein the hydrophilic organic solvent is ethanol.

13. The process for producing according to claim 1, wherein, in general formula (1), R is an alkyl group containing 1 to 4 carbon atoms.

14. The process for producing according to claim 13, wherein, in general formula (1), R is ethyl.

15. The process for producing according to claim 1, wherein, in the second step, the inorganic salt formed is potassium sulfate or calcium sulfate and this is removed by precipitation from water.

16. The process for producing according to claim 5, wherein, in the third step, the base used for the adjustment to the isoelectric point is an inorganic base selected from among alkali metal hydroxides, alkali metal carbonates, alkali metal hydrogencarbonates, alkaline earth metal hydroxides and alkaline earth metal carbonates.

17. The process for producing according to claim 4, wherein the inorganic acid used in the second step is hydrochloric acid or sulfuric acid.

18. The process for producing according to claim 5, wherein the inorganic acid used in the second step is hydrochloric acid or sulfuric acid.

19. The process for producing according to claim 6, wherein the inorganic acid used in the second step is hydrochloric acid or sulfuric acid.

20. The process for producing according to claim 7, wherein the inorganic acid used in the second step is hydrochloric acid or sulfuric acid.

* * * * *

UNITED STATES PATENT AND TRADEMARK OFFICE
CERTIFICATE OF CORRECTION

PATENT NO.    : 6,271,393 B1
DATED         : August 7, 2001
INVENTOR(S)   : Moroshima et al.

It is certified that error appears in the above-identified patent and that said Letters Patent is hereby corrected as shown below:

Column 13,
Line 11, claim 4 should read as follows:
4. The process for producing according to claim 1,
    wherein, in the second step, the inorganic acid is used in an amount within the range of over (n-1) up to n molar equivalents (n$\geq$3) and,
    in the third step, the mixture after removal of the inorganic salt is adjusted to the isoelectric point using a base in an amount of (molar equivalents of the inorganic acid used) - (n-1) molar equivalents.

Signed and Sealed this

Twenty-fifth Day of January, 2005

JON W. DUDAS
*Director of the United States Patent and Trademark Office*